(12) United States Patent
Wang

(10) Patent No.: US 10,258,404 B2
(45) Date of Patent: Apr. 16, 2019

(54) PARTIALLY COVERED JAW ELECTRODES

(71) Applicant: Gyrus ACMI, Inc., Southborough, MA (US)

(72) Inventor: Huisun Wang, Maple Grove, MN (US)

(73) Assignee: GYRUS, ACMI, INC., Southborough, MA (US)

( * ) Notice: Subject to any disclaimer, the term of this patent is extended or adjusted under 35 U.S.C. 154(b) by 867 days.

(21) Appl. No.: 14/261,131

(22) Filed: Apr. 24, 2014

(65) Prior Publication Data

US 2015/0305796 A1    Oct. 29, 2015

(51) Int. Cl.

| *A61B 17/28* | (2006.01) |
|---|---|
| *A61B 18/00* | (2006.01) |
| *A61B 18/08* | (2006.01) |
| *A61B 18/14* | (2006.01) |
| *A61B 90/00* | (2016.01) |

(52) U.S. Cl.
CPC ........ *A61B 18/085* (2013.01); *A61B 18/1445* (2013.01); *A61B 17/282* (2013.01); *A61B 2018/00101* (2013.01); *A61B 2018/00589* (2013.01); *A61B 2090/0445* (2016.02)

(58) Field of Classification Search
CPC .............. A61B 18/085; A61B 18/1445; A61B 2090/0481; A61B 2017/2825; A61B 2017/2926; A61B 2090/0445
See application file for complete search history.

(56) References Cited

U.S. PATENT DOCUMENTS

| 2,575,652 A | 11/1951 | Bovee |
|---|---|---|
| 3,576,072 A | 4/1971 | Foster |
| 3,818,784 A | 6/1974 | McClure |
| 4,041,952 A | 8/1977 | Morrison, Jr. et al. |
| 4,171,700 A | 10/1979 | Farin |
| 4,202,337 A | 5/1980 | Hren et al. |
| 4,375,218 A | 3/1983 | DiGeronimo |
| 4,407,069 A | 10/1983 | Conners |
| 4,462,759 A | 7/1984 | McGeehee |
| 4,492,231 A | 1/1985 | Auth |
| 4,492,832 A | 1/1985 | Taylor |
| 4,504,707 A | 3/1985 | Ochiai |
| 4,524,648 A | 6/1985 | Chung |
| 4,552,143 A | 11/1985 | Lottick |
| 4,669,470 A | 6/1987 | Brandfield |

(Continued)

FOREIGN PATENT DOCUMENTS

EP    1977707 A1    10/2008

*Primary Examiner* — Linda C Dvorak
*Assistant Examiner* — Annabeth E Rodriguez

(57) ABSTRACT

An electrosurgical device includes a pair of jaws including a first jaw disposed adjacent to a second jaw. The pair of jaws is movable between open and closed positions. Each jaw comprises an electrode, and each jaw has an active surface. The first jaw active surface is disposed adjacent to the second jaw active surface in the closed position. An actuating member is coupled to one or more of the first and second jaws. The actuating member is configured to move the pair of jaws between the open position and the closed position. In one form, an insulating ring is disposed around the first jaw. In another form, a shield system is disposed on first and second side surfaces of the first jaw and a portion of the first jaw active surface. In yet another form, the shield system forms a lip extending from the first jaw.

8 Claims, 4 Drawing Sheets

(56) References Cited

U.S. PATENT DOCUMENTS

| | | |
|---|---|---|
| 4,713,885 A | 12/1987 | Keklark et al. |
| 4,757,612 A | 7/1988 | Peyrot |
| 4,784,136 A | 11/1988 | Klein |
| 4,860,745 A | 8/1989 | Farin et al. |
| 5,021,616 A | 6/1991 | Hardt |
| 5,035,695 A | 7/1991 | Weber, Jr. et al. |
| 5,071,426 A | 12/1991 | Dolgin et al. |
| 5,108,392 A | 4/1992 | Spingler |
| 5,196,009 A | 2/1993 | Kirwan, Jr. |
| 5,190,541 A | 3/1993 | Abele et al. |
| 5,207,696 A | 5/1993 | Matwijcow |
| 5,208,983 A | 5/1993 | Masse |
| 5,226,904 A | 7/1993 | Gentelia et al. |
| 5,281,216 A | 1/1994 | Klicek |
| 5,290,286 A | 3/1994 | Parins |
| 5,342,359 A | 8/1994 | Rydell |
| 5,403,312 A | 4/1995 | Yates et al. |
| 5,423,814 A | 6/1995 | Zhu et al. |
| 5,440,813 A | 8/1995 | Roskam |
| 5,441,498 A | 8/1995 | Perkins |
| 5,445,638 A | 8/1995 | Rydell et al. |
| 5,427,442 A | 12/1995 | Klicek |
| 5,531,744 A | 7/1996 | Nardella et al. |
| 5,540,685 A | 7/1996 | Parins et al. |
| 5,562,503 A | 10/1996 | Ellman et al. |
| 5,573,424 A | 11/1996 | Poppe |
| 5,626,577 A | 5/1997 | Harris |
| 5,702,390 A | 12/1997 | Austin et al. |
| 5,709,680 A | 1/1998 | Yates et al. |
| 5,735,849 A | 4/1998 | Baden et al. |
| 5,779,701 A | 7/1998 | McBrayer et al. |
| H1745 H * | 8/1998 | Paraschac ............ A61B 18/1447 606/51 |
| 5,810,805 A | 9/1998 | Sutcu et al. |
| 5,827,281 A * | 10/1998 | Levin ................ A61B 18/1445 606/170 |
| 5,891,140 A | 4/1999 | Ginn et al. |
| 5,902,301 A | 5/1999 | Olig |
| 5,951,545 A | 9/1999 | Schilling et al. |
| 6,024,741 A | 2/2000 | Williamson, IV et al. |
| 6,030,384 A | 2/2000 | Nezhat |
| 6,039,734 A | 3/2000 | Goble |
| 6,074,386 A | 6/2000 | Gobel et al. |
| 6,086,586 A | 7/2000 | Hooven |
| 6,102,909 A | 8/2000 | Chen et al. |
| 6,110,171 A | 8/2000 | Rydell |
| 6,113,596 A | 9/2000 | Hooven et al. |
| 6,152,923 A | 11/2000 | Ryan |
| 6,190,386 B1 | 2/2001 | Rydell |
| 6,270,497 B1 | 8/2001 | Sekino et al. |
| 6,325,795 B1 | 12/2001 | Lindemann et al. |
| 6,358,268 B1 | 3/2002 | Hunt et al. |
| 6,402,747 B1 | 6/2002 | Lindemann et al. |
| 6,428,538 B1 | 8/2002 | Blewett et al. |
| 6,458,128 B1 | 10/2002 | Schulze |
| 6,458,130 B1 | 10/2002 | Frazier et al. |
| 6,464,704 B2 | 10/2002 | Schmaltz et al. |
| 6,486,419 B2 | 11/2002 | Horiguchi et al. |
| 6,514,252 B2 | 2/2003 | Nezhat et al. |
| 6,551,313 B1 | 4/2003 | Levin |
| 6,619,038 B2 | 9/2003 | Takada et al. |
| 6,623,499 B1 | 9/2003 | Andreini et al. |
| 6,652,514 B2 | 11/2003 | Ellman et al. |
| 6,679,882 B1 | 1/2004 | Kornerup |
| 6,695,840 B2 | 2/2004 | Schulze |
| 6,726,686 B2 | 4/2004 | Buysse et al. |
| 6,749,610 B2 | 6/2004 | Kirwan, Jr. et al. |
| 6,752,767 B2 | 6/2004 | Turovskiy et al. |
| 6,808,525 B2 | 10/2004 | Latterell et al. |
| 6,827,717 B2 | 12/2004 | Brommersma et al. |
| 6,860,882 B2 | 3/2005 | Battles et al. |
| 6,926,716 B2 | 8/2005 | Baker et al. |
| 6,942,662 B2 | 9/2005 | Goble et al. |
| 7,083,613 B2 | 8/2006 | Treat |
| 7,094,231 B1 | 8/2006 | Ellman et al. |
| 7,112,199 B2 | 9/2006 | Cosmescu |
| 7,135,020 B2 * | 11/2006 | Lawes ................ A61B 18/1445 606/50 |
| 7,156,846 B2 | 1/2007 | Dycus et al. |
| 7,160,298 B2 * | 1/2007 | Lawes .................... A61B 18/14 606/50 |
| 7,232,440 B2 | 6/2007 | Dumbauld et al. |
| 7,244,257 B2 | 7/2007 | Podhajsky et al. |
| 7,252,667 B2 | 8/2007 | Moses et al. |
| 7,344,536 B1 | 3/2008 | Lunsford et al. |
| 7,367,976 B2 | 5/2008 | Lawes et al. |
| 7,481,810 B2 | 1/2009 | Dumbauld et al. |
| 7,503,917 B2 | 3/2009 | Sartor et al. |
| 7,604,635 B2 | 10/2009 | McClurken et al. |
| 7,674,261 B2 | 3/2010 | Garito et al. |
| 7,722,607 B2 | 5/2010 | Dumbauld et al. |
| 7,749,222 B2 | 7/2010 | Lu et al. |
| 7,753,909 B2 | 7/2010 | Chapman et al. |
| 7,758,577 B2 | 7/2010 | Nobis et al. |
| 7,776,036 B2 | 8/2010 | Schechter et al. |
| 7,799,026 B2 * | 9/2010 | Schechter ............ A61B 17/122 606/49 |
| 7,879,038 B2 | 2/2011 | Reiley et al. |
| 7,896,875 B2 | 3/2011 | Heim et al. |
| 7,909,820 B2 | 3/2011 | Lipson et al. |
| 7,922,718 B2 | 4/2011 | Moses et al. |
| 7,922,953 B2 * | 4/2011 | Guerra ................ A61B 18/1445 264/259 |
| 7,931,668 B2 | 4/2011 | Sloat |
| 7,938,469 B2 | 5/2011 | Ait-Mani |
| 7,942,872 B2 | 5/2011 | Ein-Gal |
| 7,951,150 B2 | 5/2011 | Johnson et al. |
| 7,955,331 B2 | 6/2011 | Truckai et al. |
| 8,062,292 B1 | 11/2011 | Slater |
| 8,100,894 B2 | 1/2012 | Mucko et al. |
| 8,162,940 B2 | 4/2012 | Johnson et al. |
| 8,211,105 B2 * | 7/2012 | Buysse ................ A61B 18/1445 606/41 |
| 8,216,231 B2 | 7/2012 | Behl et al. |
| 8,226,649 B2 | 7/2012 | Falkenstein et al. |
| 8,241,284 B2 | 8/2012 | Dycus et al. |
| 8,251,989 B1 | 8/2012 | Newton et al. |
| 8,262,655 B2 | 9/2012 | Ghabrial et al. |
| 8,298,228 B2 * | 10/2012 | Buysse ............... A61B 18/1442 606/41 |
| 8,394,095 B2 | 3/2013 | Garrison et al. |
| 8,512,336 B2 * | 8/2013 | Couture ............. A61B 18/1445 606/45 |
| 8,568,408 B2 | 10/2013 | Townsend et al. |
| 8,814,864 B2 * | 8/2014 | Gilbert ................ A61B 18/1445 606/51 |
| 9,023,044 B2 * | 5/2015 | Emmerich .......... A61B 18/1445 606/42 |
| 9,095,347 B2 * | 8/2015 | Shields ............... A61B 18/1442 |
| 9,113,882 B2 * | 8/2015 | Twomey ............. A61B 18/1445 |
| 2003/0181904 A1 | 9/2003 | Levine et al. |
| 2004/0030330 A1 | 2/2004 | Brassell et al. |
| 2005/0013827 A1 | 1/2005 | Busfield |
| 2005/0021025 A1 * | 1/2005 | Buysse ............... A61B 18/1442 606/51 |
| 2005/0113825 A1 | 5/2005 | Cosmescu |
| 2005/0187512 A1 | 8/2005 | Isola et al. |
| 2006/0084973 A1 | 4/2006 | Hushka |
| 2006/0111711 A1 | 5/2006 | Goble |
| 2006/0217701 A1 | 9/2006 | Young et al. |
| 2006/0217709 A1 | 9/2006 | Couture |
| 2006/0271042 A1 | 11/2006 | Laterell et al. |
| 2007/0123855 A1 | 5/2007 | Morley et al. |
| 2008/0033428 A1 | 2/2008 | Artale et al. |
| 2008/0147092 A1 | 6/2008 | Rogge et al. |
| 2008/0236860 A1 | 10/2008 | Howe |
| 2008/0249527 A1 * | 10/2008 | Couture ............. A61B 18/1442 606/51 |
| 2008/0287948 A1 | 11/2008 | Newton et al. |
| 2009/0062786 A1 | 3/2009 | Garito et al. |
| 2009/0062792 A1 | 3/2009 | Vakharia |
| 2009/0093804 A1 | 4/2009 | Newton |
| 2009/0138013 A1 | 5/2009 | Thorne et al. |

(56) References Cited

U.S. PATENT DOCUMENTS

| | | |
|---|---|---|
| 2010/0042096 A1 | 2/2010 | Ellman |
| 2010/0087814 A1 | 4/2010 | Desinger et al. |
| 2011/0054462 A1 | 3/2011 | Ellman |
| 2011/0077648 A1 | 3/2011 | Lee et al. |
| 2011/0112530 A1 | 5/2011 | Keller |
| 2011/0178515 A1 | 7/2011 | Bloom et al. |
| 2011/0224669 A1 | 9/2011 | Podany |
| 2012/0101501 A1 | 4/2012 | Nishimura et al. |
| 2012/0123405 A1 | 5/2012 | Moua et al. |
| 2013/0079762 A1 | 3/2013 | Twomey et al. |
| 2013/0178852 A1 | 7/2013 | Allen, IV et al. |
| 2013/0226178 A1 | 8/2013 | Brandt |

\* cited by examiner

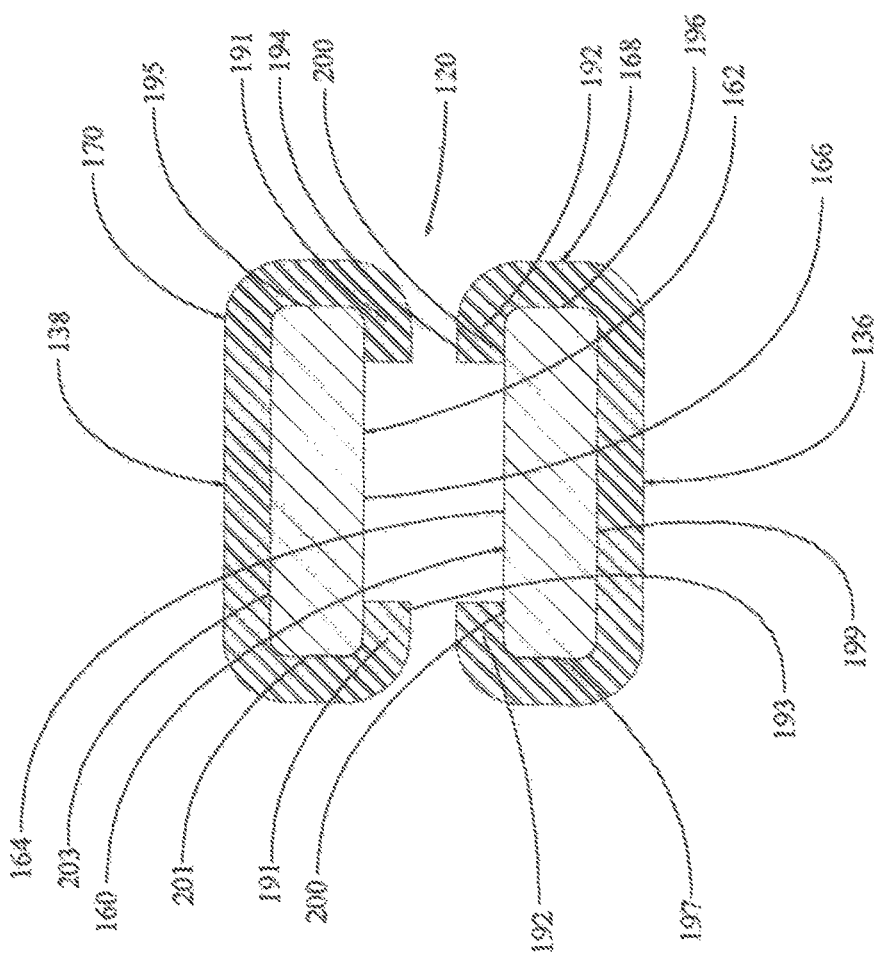
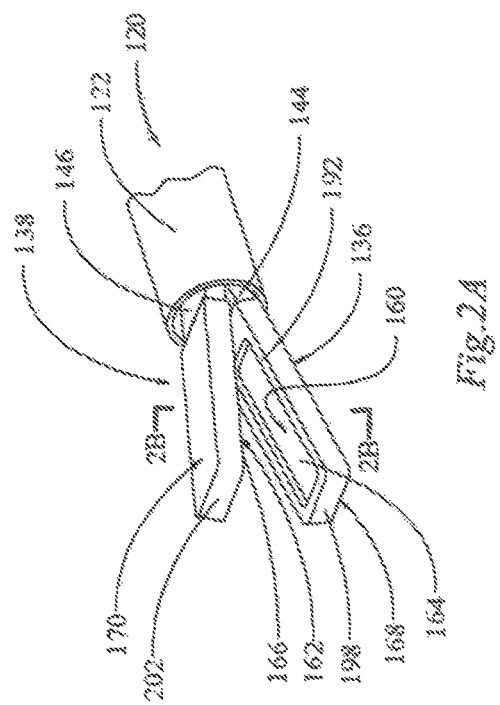
Fig. 2A
Fig. 2B

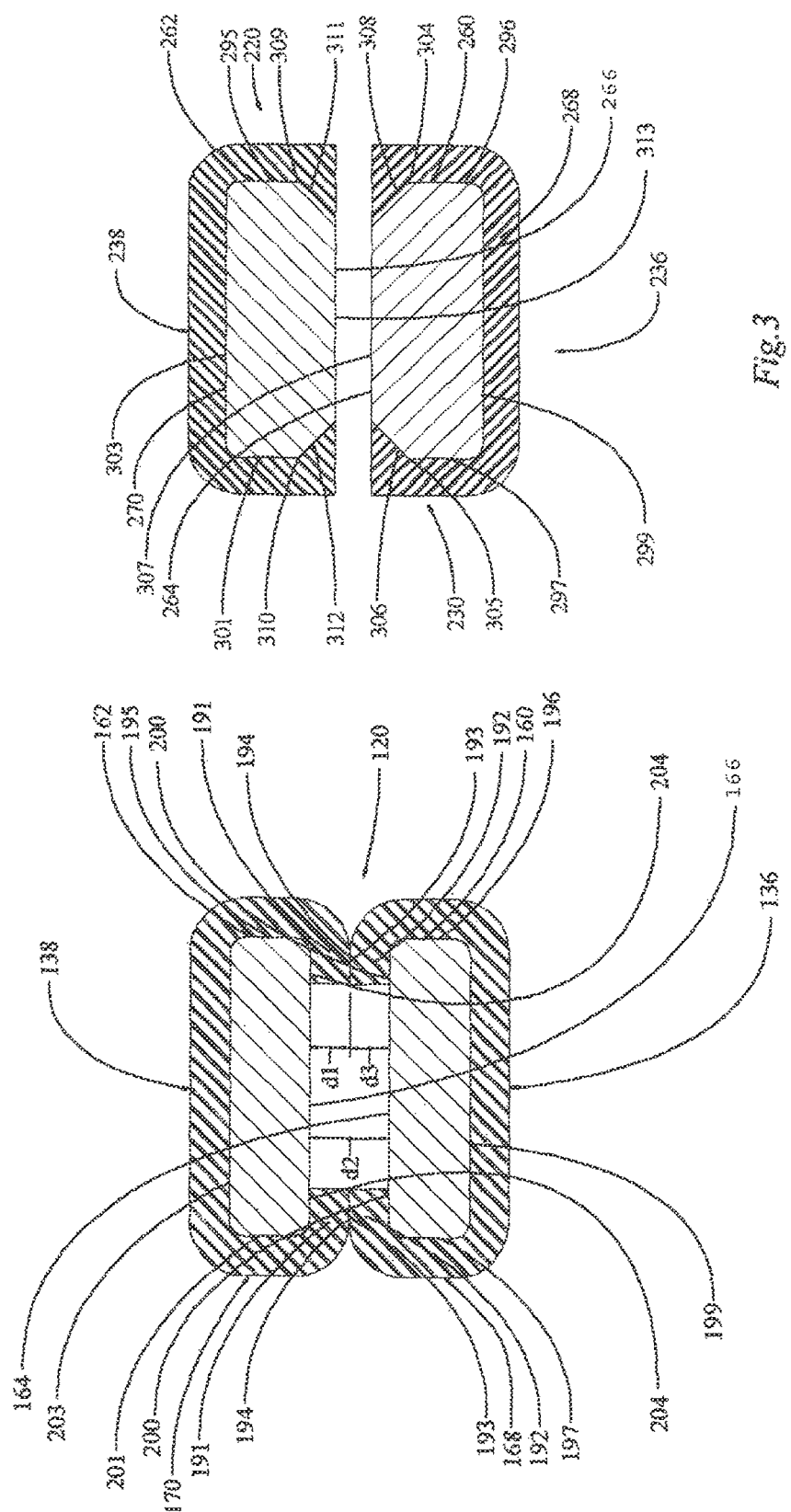

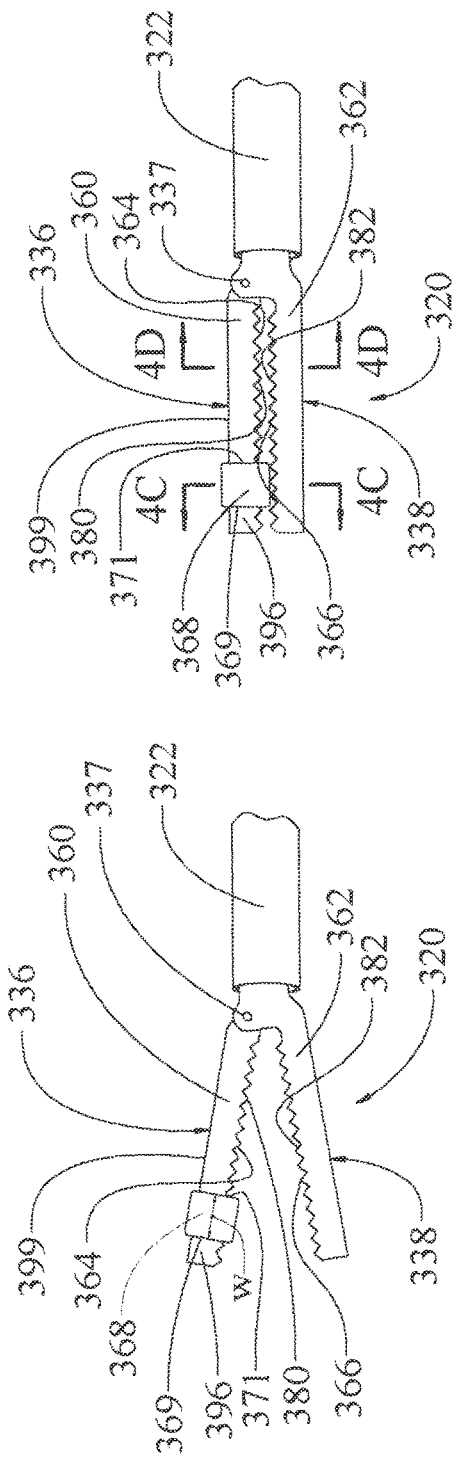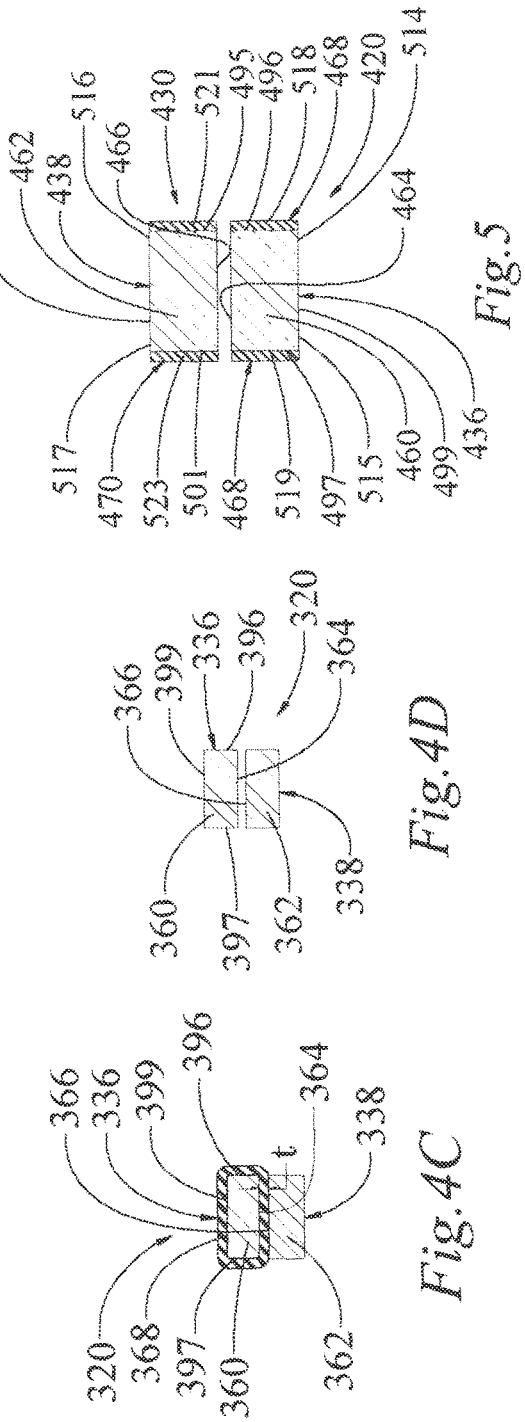

PARTIALLY COVERED JAW ELECTRODES

FIELD

The present disclosure relates to surgical devices, and more particular, surgical devices having opposed members that may be used for gripping or applying a current.

BACKGROUND

The statements in this section merely provide background information related to the present disclosure and may or may not constitute prior art.

Surgical forceps or tweezers are used in various applications during medical therapy procedures. Such devices are commonly used for holding or gripping objects.

Recently, medical practitioners have also used bipolar forceps and tweezers during surgical procedures. Bipolar forceps and tweezers may be used to seal vessels by delivering pulsed bipolar energy to coagulate nearby tissue, which may replace or minimize the need for sutures and staples.

Thermal margin, thermal injury and re-grasp may present issues when using electrosurgical devices, such as electrosurgical forceps. The thermal margin is the heat spread during coagulation to cause excess tissue effect. For example, energy may emanate from the non-active surfaces of the electrode, or the outside faces, which may cause the thermal margin to reach beyond the area intended to be treated. Thermal injury may be caused by residual heat on the jaws after a coagulation cycle. Residual heat on the jaws could cause unwanted injury if the jaws contact surrounding tissue and/or organs. Re-grasp involves the electrical short between a pair of jaw electrodes when treating thin tissues. Such shorting typically turns on a "re-grasp" alarm and shuts down the coagulation function.

Accordingly, there exists a need for electrosurgical devices that limit excess thermal margin, thermal injury, and electrical shorting or re-grasp.

SUMMARY

The present disclosure provides an electrosurgical device having a pair of electrosurgical jaws and an insulating shield system. The insulating shield system may be configured to prevent excess thermal margin, thermal injury, and/or electrical short or re-grasp.

Accordingly, pursuant to one aspect of the invention, there is contemplated an electrosurgical device comprising a pair of jaws including a first jaw and a second jaw. The second jaw is disposed adjacent to the first jaw, and the pair of jaws is movable between an open position and a closed position. The first jaw comprises a first electrode, and the second jaw comprises a second electrode. The first jaw has a first jaw active surface, and the second jaw has a second jaw active surface. The first jaw active surface is disposed adjacent to the second jaw active surface in the closed position. The first jaw has a first jaw first side surface and a first jaw second side surface. The first jaw first side surface is disposed adjacent to a first side of the first jaw active surface, and the first jaw second side surface is disposed adjacent to a second side of the first jaw active surface. The second jaw has a second jaw first side surface and a second jaw second side surface. The second jaw first side surface is disposed adjacent to a first side of the second jaw active surface, and the second jaw second side surface is disposed adjacent to a second side of the second jaw active surface. An actuating member is coupled to at least one of the first and second jaws. The actuating member is configured to move the pair of jaws between the open position and the closed position. A first insulating shield system is disposed on the first jaw first side surface and the first jaw second side surface. The first insulating shield system includes an insulating material. The first jaw active surface has a first jaw first portion covered by the first insulating shield system and a first jaw second portion at least substantially free from contact with the first insulating shield system. A second insulating shield system is disposed on the second jaw first side surface and the second jaw second side surface. The second insulating shield system also includes an insulating material. The second jaw active surface has a second jaw first portion covered by the second insulating shield system and a second jaw second portion at least substantially free from contact with the second insulating shield system. The first and second electrodes are configured to deliver an energy to a tissue.

Accordingly, pursuant to another aspect of the invention, there is contemplated an electrosurgical device comprising a pair of jaws including a first jaw and a second jaw, the second jaw being disposed adjacent to the first jaw. The pair of jaws is movable between an open position and a closed position. The first jaw comprises a first electrode, and the second jaw comprises a second electrode. The first jaw has a first jaw active surface, and the second jaw has a second jaw active surface. The first jaw active surface is disposed adjacent to the second jaw active surface in the closed position. An actuating member is coupled to at least one of the first and second jaws. The actuating member is configured to move the pair of jaws between the open position and the closed position. An insulating shield system is disposed around the first jaw active surface. The first jaw active surface has at least a portion substantially free from contact with the insulating shield system. The insulating shield system includes an insulating material. The insulating shield system forms a lip extending from the first jaw. The lip is disposed a first distance from the second jaw active surface in the closed position. The first jaw active surface is disposed a second distance from the second jaw active surface in the closed position. The first distance is smaller than the second distance. The first and second electrodes are configured to deliver and energy to a tissue.

Accordingly, pursuant to yet another aspect of the invention, there is contemplated an electrosurgical device comprising a pair of jaws including a first jaw and a second jaw, the second jaw being disposed adjacent to the first jaw. The pair of jaws is movable between an open position and a closed position. The first jaw comprises a first electrode, and the second jaw comprises a second electrode. The first jaw has a first jaw active surface, and the second jaw has a second jaw active surface. The first jaw active surface is disposed adjacent to the second jaw active surface in the closed position. An actuating member is coupled to at least one of the first and second jaws. The actuating member is configured to move the pair of jaws between the open position and the closed position. An insulating ring is disposed around the first jaw. The first and second electrodes are configured to deliver an energy to a tissue.

The invention may be further characterized by one or any combination of the features described herein, such as: the first jaw active surface having a first jaw main face connected to a first jaw first angled face and a first jaw second angled face; the first jaw first angled face connecting the first jaw main face to the first jaw first side surface; the first jaw second angled face connecting the first jaw main face to the first jaw second side surface; the second jaw active surface having a second jaw main face connected to a second jaw first angled face and a second jaw second angled face; the second jaw first angled face connecting the second jaw main face to the second jaw first side surface; the second jaw second angled face connecting the second jaw main face to the second jaw second side surface; the first insulating shield system covering the first jaw first and second angled faces; the second insulating shield system covering the second jaw first and second angled faces; the first jaw main face being substantially free from contact with the first insulating shield system; the second jaw main face being substantially free from contact with the second insulating shield system; the first jaw further comprising a first jaw outside surface connected to the first jaw first and second side surfaces; the first insulating shield system covering the first jaw outside surface; the second jaw further comprising a second jaw outside surface connected to the second jaw first and second side surfaces; the second insulating shield system covering the second jaw outside surface; the first and second insulating shield systems each comprising at least one of ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and nylon; further comprising a first member connected to the first jaw and a second member connected to the second jaw; further comprising a tube configured to surround the first and second members to pivot the first jaw with respect to the second jaw; the first jaw active surface being recessed with respect to the lip of the insulating shield system; the first jaw further comprising a first jaw outside surface disposed on an opposite side of the first jaw from the first jaw active surface; the first jaw further comprising two first jaw side surfaces; each first jaw side surface of the two first jaw side surfaces connecting the first jaw active surface to the first jaw outside surface; the insulating shield system substantially covering the first jaw outside surface and each of the first jaw side surfaces; the first jaw further comprising a first jaw end surface connecting the two first jaw side surfaces; the insulating shield system substantially covering the first jaw end surface; wherein the insulating shield system is a first insulating shield system and the lip is a first lip, the electrosurgical device further comprising a second insulating shield system disposed around the second jaw active surface, the second jaw active surface having at least a portion substantially free from contact with the second insulating shield system, the second insulating shield system comprising an insulating material, the second insulating shield system forming a second lip extending from the second jaw; the second jaw active surface being recessed with respect to the second lip; the second lip being disposed a third distance from the first jaw active surface in the closed position; the third distance being smaller than the second distance; the second jaw further comprising a second jaw outside surface disposed on an opposite side of the second jaw from the second jaw active surface; the second jaw further comprising two second jaw side surfaces; each second jaw side surface of the two second jaw side surfaces connecting the second jaw active surface to the second jaw outside surface; the second insulating shield system substantially covering the second jaw outside surface and each of the second jaw side surfaces; and the first jaw further comprising a first jaw outside surface disposed on an opposite side of the first jaw from the first jaw active surface, the insulating ring extending around the first jaw active surface and the first jaw outside surface.

Further aspects, advantages and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

FIG. 2A is a perspective view of a portion of another electrosurgical device in an open position, according to the principles of the present disclosure;

FIG. 2B is a cross-sectional view of the electrosurgical device of FIG. 2A in the open position, taken along the lines 2B-2B, according to the principles of the present disclosure;

FIG. 2C is a cross-sectional view of the electrosurgical device of FIGS. 2A-2B in a closed position, in accordance with the principles of the present disclosure;

FIG. 3 is a cross-sectional view of yet another electrosurgical device in an open position, according to the principles of the present disclosure;

FIG. 4A is a side view of a portion of still another electrosurgical device in an open position, in accordance with the principles of the present disclosure;

FIG. 4B is a side view of the portion of the electrosurgical device of FIG. 4A in a closed position, according to the principles of the present disclosure;

FIG. 4C is a cross-sectional view the electrosurgical device of FIGS. 4A-4B in the closed position, taken along the lines 4C-4C in FIG. 4B, in accordance with the principles of the present disclosure;

FIG. 4D is a cross-sectional view the electrosurgical device of FIGS. 4A-4C in the closed position, taken along the lines 4D-4D in FIG. 4B, according to the principles of the present disclosure; and FIG. 5 is a cross-sectional view of a still another electrosurgical device in an open position, according to the principles of the present disclosure.

DETAILED DESCRIPTION

Figure 1:
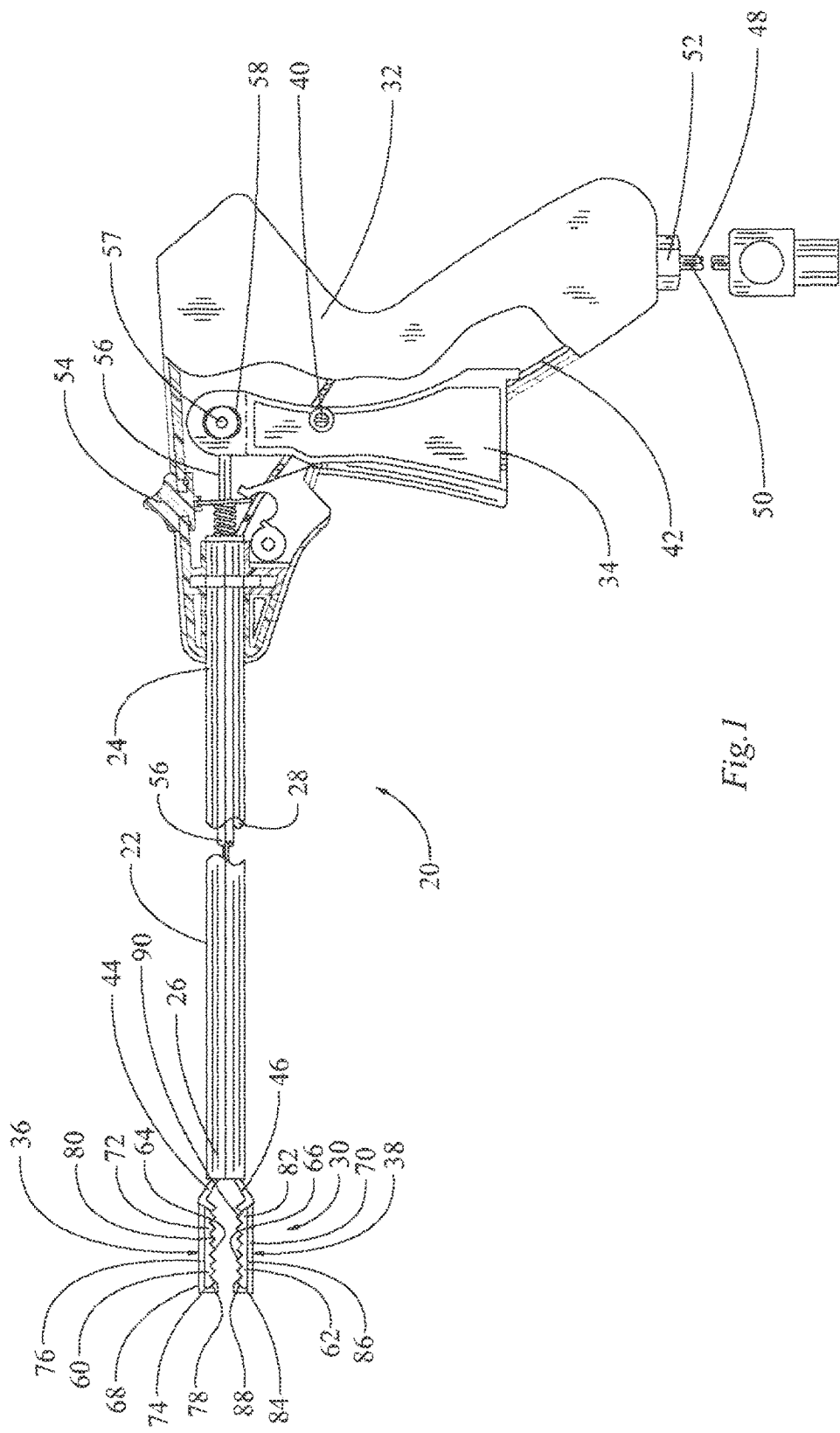
FIG. 1 is a side elevation of an electrosurgical device in an open position, in accordance with the principles of the present disclosure.

The following description is merely exemplary in nature and is not intended to limit the present disclosure, application, or uses.

The present disclosure provides an electrosurgical device having a pair of electrosurgical jaws and an insulating shield system. The insulating shield system may be configured to prevent excess thermal margin, thermal injury, and/or electrical short or re-grasp.

For example, referring to FIG. 1, an electrosurgical forceps is illustrated and generally designated at 20. The forceps 20 are of the electrosurgical type that may be used as a bipolar device, for example, to apply pulsed or non-pulsed energy to coagulate a tissue. The electrosurgical forceps 20 may be used, for example, in percutaneous laparoscopic surgical procedures.

The electrosurgical forceps 20 may include an elongate tubular outer member 22, which may be formed from a variety of materials, such as stainless steel. The outer member 22 has a proximal end 24, a distal end 26, and a lumen 28 extending along the length of the outer member 22. A coagulating jaw arrangement 30 extends from the distal end 26 of the outer member 22.

A handle 32 is located at the proximal end 24 of the outer member 22. The handle 32 includes a lever 34 that may be pressed to actuate the coagulating jaws 36, 38 of the jaw arrangement 30. The lever 34 may be pivotally secured to the device 20 through a pivot pin 40. A torsion spring (partially shown at numeral 42) is located in the handle 32 and acts as a biasing means to provide a return force for the lever 34.

A first conductive electrical lead part 44 is connected to, or integrally formed with, the first forceps jaw 36, and a second conductive electrical lead part 46 is connected to, or integrally formed with, the second forceps jaw 38. The conductive lead parts 44, 46 are electrically connected to a pair of insulated electrical leads 48, 50 extending from an electrical connector 52 disposed on the handle 32; thus, the lead parts 44, 46 may be connected to, or formed with, wires or other conductive parts (not shown) that extend through the length of the outer member 22 and through the handle 32 to the insulated leads 48, 50. The leads 48, 50 are configured to be connected to a source of RF power (not shown).

In some versions, a thumb slide 54 may be included at the top of the handle 32 for selecting a unidirectional or bidirectional mode of the forceps movement. For example, the thumb slide 54 may be moved into a first position for unidirectional movement of the jaw arrangement 30, wherein each jaw 36, 38 can only move toward each other to close on the tissue to be grasped and coagulated. In the unidirectional mode, if pressure on the lever 34 is released, the jaws 36, 38 remain in the position they were in when the pressure was released. The thumb slide 54 may be moved into a second position for bidirectional movement of the jaw arrangement 30, wherein the jaws 36, 38 can move in both directions to close or open. In the bidirectional mode, when the lever 34 is released, the jaws 36, 38 open under the influence of the return spring 42.

An inner tubular member 56 is connected to a clevis pin arrangement 57, which is coupled to the lever 34 through a slot 58 formed in an upper part of the lever 34. The inner tubular member 56 extends through the outer member 22 and is coupled to the first and second jaws 36, 38 through the arcuate leads 44, 46 at the distal end 26 of the outer member 22. The lever 34 is configured to move the inner tubular member 56 in an axial direction. Accordingly, the arcuate leads 44, 46 are moved into and out of the lumen 28 of the outer member 22, and/or the arcuate leads 44, 46 may be moved into and out of the inner member 56 or another sleeve to squeeze the leads 44, 46 and/or the jaws 36, 38 toward each other. As such, the lever 34 actuates the first and second jaws 36, 38 through the inner tubular member 56.

The first jaw 36 is disposed adjacent to the second jaw 38, and they are movable between an open position and a closed position, as described above or in any suitable manner. The first jaw 36 comprises a first electrode 60, and the second jaw 38 comprises a second electrode 62. The electrodes 60, 62 are configured to deliver an energy, or apply a current, to a tissue when energized. The first and second electrodes 60, 62 may be active bipolar electrodes that are configured to be coupled with and energized by an electrode energy source. In the illustrated example, the current may be provided through the leads 48, 50 to the leads 44, 46, and ultimately to the first and second electrodes 60, 62.

The first jaw 36 has a first electrode active surface 64, and the second jaw 38 has a second electrode active surface 66. The first electrode active surface 64 is disposed adjacent to the second electrode active surface 66. In the closed position, the first electrode active surface 64 is disposed adjacent to and contacting a first side of a tissue, and the second electrode active surface 66 is disposed adjacent to and contacting a second side of a tissue, the first and second jaws 36, 38 grasping the tissue. Accordingly, when a tissue is grasped between the active surfaces 64, 66, a current may be applied to the tissue through the active surfaces 64, 66.

A first insulating shield 68 is disposed on the first jaw 36, partially covering the first electrode 60. The first insulating shield 68 covers a portion of the side surfaces (one side designated at 72), the end surface 74, and the outside surface 76 of the first electrode 60. In addition, the first insulating shield 68 covers a portion of the active surface 64; more particularly, a distal portion 78 of the active surface 64 is insulated by the first insulating shield 68. In this example, the active surface 64 has a plurality of teeth 80 disposed thereon.

A second insulating shield 70 is disposed on the second jaw 38, partially covering the second electrode 62. The second insulating shield 70 covers a portion of the side surfaces (one side designated at 82), the end surface 84, and the outside surface 86 of the second electrode 62. In addition, the second insulating shield 70 covers a portion of the active surface 66; more particularly, a distal portion 88 of the active surface 66 is insulated by the second insulating shield 70. In this example, the active surface 66 has a plurality of teeth 90 disposed thereon.

The first and second insulating shields 68, 70 are formed of an insulating material, such as rubber. In some variations, the first and second insulating shields 68, 70 could comprise, for example, ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and/or nylon.

Though first and second insulating shields 68, 70 are illustrated, it should be understood that, in some variations, only one of the insulating shields 68, 70 is present.

Referring now to FIGS. 2A-2C, another variation of an electrosurgical forceps is illustrated and generally designated at 120. Like the forceps 20 described above, the forceps 120 are of the electrosurgical type that may be used as a bipolar device, for example, to apply pulsed or non-pulsed energy to coagulate a tissue. All details not described with respect to FIGS. 2A-2C may be similar or the same as the features described with respect to the example in FIG. 1 or one of the other examples given herein. For example, the handle and actuation assembly are not illustrated in FIGS. 2A-2C, but it should be understood that the forceps 120 could be actuated in any suitable manner, such as described with respect to FIG. 1.

A first jaw 136 and a second jaw 138 extend from an outer member 122. A first conductive lead 144 is connected to the first forceps jaw 136, and a second conductive lead 146 is connected to the second forceps jaw 138. The leads 144, 146 are configured to be connected to a source of RF power (not shown).

The first jaw 136 is disposed adjacent to the second jaw 138, and they are movable between an open position and a closed position, as described above or in any suitable manner. In both FIGS. 2A and 2B, the jaws 136, 138 are illustrated in the open position. In FIG. 2C, the jaws 136, 138 are illustrated in the closed position. The first jaw 136 comprises a first electrode 160, and the second jaw 138 comprises a second electrode 162 (hidden behind second insulating shield 170 in FIG. 2A). The electrodes 160, 162 are configured to deliver an energy, or apply a current, to a tissue when energized. The first and second electrodes 160, 162 may be active bipolar electrodes that are configured to be coupled with and energized by an electrode energy source. In the illustrated example, the current may be provided through the leads 144, 146, and ultimately to the first and second electrodes 160, 162.

The first jaw 136 has a first electrode active surface 164, and the second jaw 138 has a second electrode active surface 166. The first electrode active surface 164 is disposed adjacent to the second electrode active surface 166. In the closed position, the first electrode active surface 164 is disposed adjacent to and contacting a first side of a tissue, and the second electrode active surface 166 is disposed adjacent to and contacting a second side of a tissue, the first and second jaws 136, 138 grasping the tissue. Accordingly, when a tissue is grasped between the active surfaces 164, 166, a current may be applied to the tissue through the active surfaces 164, 166.

A first insulating shield 168 is disposed around the first jaw 136, partially covering the first electrode 160. The first active surface 164 has at least a portion that is substantially free from contact with the first insulating shield 168, which is the portion that is open and facing the second active surface 166. Thus, a portion of the active surface 164 remains uncovered by the first insulating shield 168. The first insulating shield 168 forms a lip 192 extending from the first jaw 136. Referring to FIG. 2C, the lip 192 is disposed a first distance d1 from the second active surface 166 in the closed position. The first active surface 164 is disposed a second distance d2 from the second active surface 166 in the closed position. The first distance d1 is smaller or less than the second distance d2. Thus, the first active surface 164 is recessed with respect to an outer edge 194 of the lip 192.

The first insulating shield 168 also covers side surfaces 196, 197, the end surface (hidden behind an end 198 of the first insulating shield in FIG. 2A), and the outside surface 199 of the first electrode 160. The outside surface 199 is disposed on an opposite side of the first jaw 136 from the first active surface 164. Each side surface 196, 197 connects the first active surface 164 to the outside surface 199. The end surface (under shield end 198) connects each of the side surfaces 196, 197 to each other. The first insulating shield 168 substantially covers the outside surface 199 and each of the side surfaces 196, 197 and the end surface. In addition, in this example, the first insulating shield 168 covers portions 200 of the active surface 164, which are disposed under the lip 192. In this example, the active surface 164 is flat with no teeth disposed thereon; however, it should be understood that any other suitable surface could be used.

A second insulating shield 170 is disposed around the second jaw 138, partially covering the second electrode 162. The second active surface 166 has at least a portion that is substantially free from contact with the second insulating shield 170, which is the portion that is open and facing the first active surface 164. Thus, a portion of the active surface 166 remains uncovered by the second insulating shield 170. The second insulating shield 170 forms a lip 191 extending from the second jaw 138. Referring to FIG. 2C, the lip 191 is disposed a third distance d3 from the first active surface 164 in the closed position. In some examples, the magnitude of d3 may be equal to the magnitude of d1. As stated above, the second active surface 166 is disposed a distance d2 from the first active surface 164 in the closed position. The third distance d3 is smaller or less than the second distance d2.

Thus, the second active surface 166 is recessed with respect to an outer edge 193 of the lip 191.

The second insulating shield 170 also covers side surfaces 195, 201, the end surface (hidden behind an end 202 of the first insulating shield in FIG. 2A), and the outside surface 203 of the second electrode 162. The outside surface 203 is disposed on an opposite side of the second jaw 138 from the second active surface 166. Each side surface 195, 201 connects the second active surface 166 to the outside surface 203. The end surface (under shield end 202) connects each of the side surfaces 195, 201 to each other. The second insulating shield 170 substantially covers the outside surface 203 and each of the side surfaces 195, 201 and the end surface. In addition, in this example, the second insulating shield 170 covers portions 204 of the active surface 166, which are disposed under the lip 191. In this example, the active surface 166 is flat with no teeth disposed thereon; however, it should be understood that any other suitable surface could be used.

The first and second insulating shields 168, 170 are formed of an insulating material, such as rubber. In some variations, the first and second insulating shields 168, 170 could comprise, for example, ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and/or nylon.

Though first and second insulating shields 168, 170 are illustrated, it should be understood that, in some variations, only one of the insulating shields 168, 170 is present.

Referring now to FIG. 3, another variation of an electrosurgical forceps is illustrated and generally designated at 220 in a cross-sectional view. Like the forceps 20, 120 described above, the forceps 220 are of the electrosurgical type that may be used as a bipolar device, for example, to apply pulsed or non-pulsed energy to coagulate a tissue. All details not described with respect to FIG. 3 may be similar or the same as the features described with respect to the example in FIG. 1 or one of the other examples given herein. For example, the handle and actuation assembly are not illustrated in FIG. 3, but it should be understood that the forceps 220 could be actuated in any suitable manner, such as described with respect to FIG. 1.

A jaw arrangement 230 is disposed at a distal end of the forceps 220. The jaw arrangement 230 includes a first jaw 236 disposed adjacent to a second jaw 238. Conductive leads (not shown) are configured connect to the first and second jaws 236, 238 to a source of RF power (not shown).

The first and second jaws 236, 238 are movable between an open position and a closed position, as described above or in any suitable manner. In FIG. 3, the jaws 236, 238 are illustrated in the open position. The first jaw 236 comprises a first electrode 260, and the second jaw 238 comprises a second electrode 262. The electrodes 260, 262 are configured to deliver an energy, or apply a current, to a tissue when energized. The first and second electrodes 260, 262 may be active bipolar electrodes that are configured to be coupled with and energized by an electrode energy source. Current may be provided through the first and second electrodes 260, 262 to a tissue that is grasped therebetween, by way of example.

The first jaw 236 has a first electrode active surface 264, and the second jaw 238 has a second electrode active surface 266. The first electrode active surface 264 is disposed adjacent to the second electrode active surface 266. In the closed position, the first electrode active surface 264 is disposed adjacent to and contacting a first side of a tissue, and the second electrode active surface 266 is disposed adjacent to and contacting a second side of a tissue, the first and second jaws 236, 238 grasping the tissue. Accordingly, when a tissue is grasped between the active surfaces 264, 266, a current may be applied to the tissue through the active surfaces 264, 266.

A first insulating shield 268 is disposed around the first jaw 236, partially covering the first electrode 260. The first active surface 264 has at least a portion that is substantially free from contact with the first insulating shield 268, which is the portion that is open and facing the second active surface 266. Thus, a portion of the active surface 264 remains uncovered by the first insulating shield 268.

The first insulating shield 268 may also cover side surfaces 296, 297, the end surface (not visible in the cross-sectional view of FIG. 3), and the outside surface 299 of the first electrode 260. The first side surface 296 is disposed adjacent to a first side 304 of the first active surface 264. The second side surface 297 is disposed adjacent to a second side 305 of the first active surface 264. The first side 304 is an edge of a first angled face 308 of the first active portion 264; in other words, the first side surface 296 is connected to the first angled face 308. The second side 305 is an edge of a second angled face 306 of the first active portion 264; in other words, the second side surface 297 is connected to the second angled face 306. The first insulating shield 268 covers the first and second angled faces, 308, 306 . The first insulating shield 268 does not cover a main face 307 of the first active surface 264; instead, the main face 307 remains substantially free from contact with the first insulating shield 268. The main face 307 is connected to each of the angled faces 306, 308. The angled faces, 308, 306 connect the main face 307 to the side surfaces 296, 297.

The outside surface 299 is disposed on an opposite side of the first jaw 236 from the first active surface 264. Each side surface 296, 297 connects the first active surface 264 to the outside surface 299. The end surface (not shown) connects each of the side surfaces 296, 297 to each other. The first insulating shield 268 substantially covers the outside surface 299 and each of the side surfaces 296, 297 and the end surface. In this example, the active surface 264 is flat with no teeth disposed thereon; however, it should be understood that any other suitable surface could be used.

A second insulating shield 270 is disposed around the second jaw 238, partially covering the second electrode 262. The second active surface 266 has at least a portion that is substantially free from contact with the second insulating shield 270, which is the portion that is open and facing the first active surface 264. Thus, a portion of the second active surface 266 remains uncovered by the second insulating shield 270.

The second insulating shield 270 may also cover side surfaces 295, 301, the end surface (not visible in the cross-sectional view of FIG. 3), and the outside surface 303 of the second electrode 262. The first side surface 295 is disposed adjacent to a first side 309 of the second active surface 266. The second side surface 301 is disposed adjacent to a second side 310 of the second active surface 266. The first side 309 is an edge of a first angled face 311 of the second active portion 266; in other words, the first side surface 295 is connected to the first angled face 311. The second side 310 is an edge of a second angled face 312 of the second active portion 266; in other words, the second side surface 301 is connected to the second angled face 312. The second insulating shield 270 covers the first and second angled faces 311, 312. The second insulating shield 270 does not cover a main face 313 of the second active surface 266; instead, the main face 313 remains substantially free from contact with the second insulating shield 270. The main face 313 is connected to each of the angled faces 311, 312. The angled faces 311, 312 connect the main face 313 to the side surfaces 295, 301.

The outside surface 303 is disposed on an opposite side of the second jaw 238 from the second active surface 266. Each side surface 295, 301 connects the second active surface 266 to the outside surface 303. The end surface (not shown) connects each of the side surfaces 295, 301 to each other. The second insulating shield 270 substantially covers the outside surface 303 and each of the side surfaces 295, 301 and the end surface. In this example, the second active surface 266 is flat with no teeth disposed thereon; however, it should be understood that any other suitable surface could be used.

The first and second insulating shields 268, 270 are formed of an insulating material, such as rubber. In some variations, the first and second insulating shields 268, 270 could comprise, for example, ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and/or nylon.

Though first and second insulating shields 268, 270 are illustrated, it should be understood that, in some variations, only one of the insulating shields 268, 270 is present. In this variation, no lip is illustrated in either of the shield portions 268, 270; however a lip could be incorporated if desired. Here, the first and second main faces 307, 313 are flush with their respective shields 268, 270 such that the main faces 307, 313 would touch in the closed position if no tissue were disposed therebetween.

Referring now to FIGS. 4A-4D, another variation of an electrosurgical forceps is illustrated and generally designated at 320. Like the forceps 20, 120, 220 described above, the forceps 320 are of the electrosurgical type that may be used as a bipolar device, for example, to apply pulsed or non-pulsed energy to coagulate a tissue. All details not described with respect to FIGS. 4A-4D may be similar or the same as the features described with respect to the example in FIG. 1 or one of the other examples given herein. For example, the handle and actuation assembly are not illustrated in FIGS. 4A-4D, but it should be understood that the forceps 320 could be actuated in any suitable manner, such as described with respect to FIG. 1.

A first jaw 336 and a second jaw 338 extend from an outer member 322. The first jaw 336 is disposed adjacent to the second jaw 338. Conductive leads (not shown) are configured connect the first and second jaws 336, 338 to a source of RF power (not shown). In the illustrated example, the first and second jaws 336, 338 are pivotally connected by a pivot pin 337, which may be insulated to prevent electrical shortage; however, the jaws 336, 338 may be coupled in any suitable way, such as that described with respect to FIG. 1.

The first and second jaws 336, 338 are movable between an open position and a closed position, as described above or in any suitable manner. In FIG. 4A, the jaws 336, 338 are illustrated in the open position. In FIGS. 4B-4D, the jaws 336, 338 are illustrated in the closed position.

The first jaw 336 comprises a first electrode 360, and the second jaw 338 comprises a second electrode 362. The electrodes 360, 362 are configured to deliver an energy, or apply a current, to a tissue when energized. The first and second electrodes 360, 362 may be active bipolar electrodes that are configured to be coupled with and energized by an electrode energy source. In the illustrated example, the current may be provided through the first and second electrodes 360, 362.

The first jaw 336 has a first electrode active surface 364, and the second jaw 338 has a second electrode active surface 366. The first electrode active surface 364 is disposed adjacent to the second electrode active surface 366. In the closed position, the first electrode active surface 364 is disposed adjacent to and contacting a first side of a tissue, and the second electrode active surface 366 is disposed adjacent to and contacting a second side of a tissue, the first and second jaws 336, 338 grasping the tissue. Accordingly, when a tissue is grasped between the active surfaces 364, 366, a current may be applied to the tissue through the active surfaces 364, 366.

An insulating ring 368 is disposed around first jaw 336. The first jaw 336 has two side surfaces 396, 397 that connect the active surface 364 to an outside surface 399. The insulating ring 368 extends around the first active surface 364, the outside surface 399, and each of the side surfaces 396, 397. The insulating ring 368 is annular having open ends 369, 371, and the ring 368 is connected all the way around the active surface 364, each side surface 396, 397, and the outside surface 399. The insulating ring 368 may have a width w in the range of about 0.010 inch to about 0.040 inch and a thickness t in the range of about 0.005 inch to about 0.015 inch, by way of example.

The insulating ring 368 prevents re-grasp and/or electrical shortage between the active surfaces 364, 366. More particularly, even when the electrode jaws 336, 338 are closed as illustrated in FIGS. 4B-4D, the active surfaces 364, 366 remain free from contact with each other. In the closed position, the insulating ring 368 contacts the second active surface 366 and acts as a stop to prevent the first active surface 364 from contacting the second active surface 366. For example, referring to FIG. 4D, the jaws 336, 338 are in the closed position, and the first and second active surfaces 364, 366 remain free from contact with each other.

In this example, each of the active surfaces 364, 366 has a plurality of teeth 380, 382 disposed thereon; however, it should be understood that a flat configuration or any other desirable configuration could be used. Although only the first electrode 360 is illustrated having an insulating ring 368 disposed therearound, it should be understood that the second electrode 362 could have its own insulating ring, or either electrode 360, 362 could have multiple insulating rings, if desired.

The insulating ring 368 is formed of an insulating material, such as rubber. In some variations, the insulating ring 368 could comprise, for example, ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and/or nylon.

Referring now to FIG. 5, another variation of an electrosurgical forceps is illustrated and generally designated at 420 in a cross-sectional view. Like the forceps 20, 120, 220, 320 described above, the forceps 420 are of the electrosurgical type that may be used as a bipolar device, for example, to apply pulsed or non-pulsed energy to coagulate a tissue. All details not described with respect to FIG. 5 may be similar or the same as the features described with respect to the example in FIG. 1 or one of the other examples given herein. For example, the handle and actuation assembly are not illustrated in FIG. 5, but it should be understood that the forceps 420 could be actuated in any suitable manner, such as described with respect to FIG. 1.

A jaw arrangement 430 is disposed at a distal end of the forceps 420. The jaw arrangement 430 includes a first jaw 436 disposed adjacent to a second jaw 438. Conductive leads (not shown) are configured connect to the first and second jaws 436, 438 to a source of RF power (not shown).

The first and second jaws 436, 438 are movable between an open position and a closed position, as described above or in any suitable manner. In FIG. 5, the jaws 436, 438 are illustrated in the open position. The first jaw 436 comprises a first electrode 460, and the second jaw 438 comprises a second electrode 462. The electrodes 460, 462 are configured to deliver an energy, or apply a current, to a tissue when energized. The first and second electrodes 460, 462 may be active bipolar electrodes that are configured to be coupled with and energized by an electrode energy source. Current may be provided through the first and second electrodes 460, 462 to a tissue that is grasped therebetween, by way of example.

The first jaw 436 has a first electrode active surface 464, and the second jaw 438 has a second electrode active surface 466. The first electrode active surface 464 is disposed adjacent to the second electrode active surface 466. In the closed position, the first electrode active surface 464 is disposed adjacent to and contacting a first side of a tissue, and the second electrode active surface 466 is disposed adjacent to and contacting a second side of a tissue, the first and second jaws 436, 438 grasping the tissue. Accordingly, when a tissue is grasped between the active surfaces 464, 466, a current may be applied to the tissue through the active surfaces 464, 466.

The first jaw 436 has an outside surface 499, a first side surface 496, and second side surface 497. The first side surface 496 connects a first side 514 of the outside surface 499 to the first active surface 464. The second side surface 497 connects a second side 515 of the outside surface 499 to the first active surface 464.

The second jaw 438 has an outside surface 503, a first side surface 495, and second side surface 501. The first side surface 495 connects a first side 516 of the outside surface 503 to the second active surface 466. The second side surface 501 connects a second side 517 of the outside surface 503 to the second active surface 466.

A first insulating shield system 468 is disposed on the first jaw 436, partially covering the first electrode 460. More specifically, the first insulating shield system 468 is disposed on the first and second side surfaces 496, 497 of the first electrode 460, wherein the first insulating shield system 468 substantially covers the first and second side surfaces 496, 497. A first shield part 518 substantially or entirely covers the first side surface 496, and a second shield part 519 substantially or entirely covers the second side surface 497.

The first active surface 464 has at least a portion that is substantially free from contact with the first insulating shield system 468; in the illustrated example, the entire active surface 464 is free from contact with the first insulating shield system 468. Thus, at least a portion of the active surface 464 remains uncovered by the first insulating shield system 468. The first outside surface 499 also has at least a portion that is substantially free from contact with the first insulating shield system 468; in the illustrated example, the entire outside surface 499 is free from contact with the first insulating shield system 468. Thus, at least a portion of the outside surface 499 remains uncovered by the first insulating shield system 468.

A second insulating shield system 470 is disposed on the second jaw 438, partially covering the second electrode 462. More specifically, the second insulating shield system 470 is disposed on the first and second side surfaces 495, 501 of the second electrode 462, wherein the second insulating shield system 470 substantially covers the first and second side surfaces 495, 501. A third shield part 521 substantially or entirely covers the first side surface 495, and a fourth shield part 523 substantially or entirely covers the second side surface 501.

The second active surface 466 has at least a portion that is substantially free from contact with the second insulating shield system 470; in the illustrated example, the entire active surface 466 is free from contact with the second insulating shield system 470. Thus, at least a portion of the active surface 466 remains uncovered by the second insulating shield system 470. The second outside surface 503 also has at least a portion that is substantially free from contact with the second insulating shield system 470; in the illustrated example, the entire outside surface 503 is free from contact with the second insulating shield system 470. Thus, at least a portion of the outside surface 503 remains uncovered by the second insulating shield system 470.

The first and second insulating shield systems 468, 470 are formed of an insulating material, such as rubber. In some variations, the first and second insulating shield systems 468, 470 could comprise, for example, ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and/or nylon.

Though first and second insulating shield systems 468, 470 are illustrated, it should be understood that, in some variations, only one of the insulating shield systems 468, 470 is present. Further, any number of the shield parts 518, 519, 521, 523 could be omitted. In this variation, no lip (as in FIGS. 2A-2C) is illustrated on either of the shield systems 468, 470; however a lip could be incorporated if desired. Here, the first and second active surfaces 464, 466 are flush with their respective shield systems 468, 470 such that the active surfaces 464, 466 would touch in the closed position if no tissue were disposed therebetween.

The description of the invention is merely exemplary in nature and variations that do not depart from the gist of the invention are intended to be within the scope of the invention. Such variations are not to be regarded as a departure from the spirit and scope of the invention. For example, variations in the various figures can be combined with each without departing from the spirit and scope of the present disclosure.

The preferred embodiment of the present invention has been disclosed. A person of ordinary skill in the art would realize, however, that certain modifications would come within the teachings of this invention. Therefore, the following claims should be studied to determine the true scope and content of the invention.

Any numerical values recited in the above application include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints, the use of "about" or "approximately" in connection with a range apply to both ends of the range. Thus, "about 20 to 30" is intended to cover "about 20 to about 30", inclusive of at least the specified endpoints.

The disclosures of all articles and references, including patent applications and publications, are incorporated by reference for all purposes.

The term "consisting essentially of" to describe a combination shall include the elements, ingredients, components or steps identified, and such other elements ingredients, components or steps that do not materially affect the basic and novel characteristics of the combination.

The use of the terms "comprising" or "including" describing combinations of elements, ingredients, components or steps herein also contemplates embodiments that consist essentially of the elements, ingredients, components or steps.

What is claimed is:

1. An electrosurgical device comprising:
    a pair of jaws including a first jaw and a second jaw, the second jaw being disposed adjacent to the first jaw, the pair of jaws being movable between an open position and a closed position, the first jaw comprising a first electrode and the second jaw comprising a second electrode, the first jaw having a first jaw active surface and the second jaw having a second jaw active surface, the first jaw active surface being disposed adjacent to the second jaw active surface in the closed position, the first jaw having a first jaw first side surface and a first jaw second side surface, the first jaw first side surface being disposed adjacent to a first side of the first jaw active surface and the first jaw second side surface being disposed adjacent to a second side of the first jaw active surface, the second jaw having a second jaw first side surface and a second jaw second side surface, the second jaw first side surface being disposed adjacent to a first side of the second jaw active surface and the second jaw second side surface being disposed adjacent to a second side of the second jaw active surface;
    an actuating member coupled to at least one of the first and second jaws, the actuating member configured to move the pair of jaws between the open position and the closed position;
    a first insulating shield system being continuous and having a uniform thickness, the first insulating shield system substantially covering a first jaw outside surface, each of the first jaw side surfaces and covering a first jaw end surface, the first insulating shield system terminating with first jaw lips that partially cover the first jaw active surface, the first insulating shield system comprising an insulating material, the first jaw active surface having a first jaw first portion covered by the first insulating shield system and a first jaw second portion at least substantially free from contact with the first insulating shield system; and a second insulating shield system being continuous and having a uniform thickness, the second insulating shield system substantially covering a second jaw outside surface, each of the second jaw side surfaces and covering a second jaw end surface, the second insulating shield system terminating with second jaw lips that partially cover the second jaw active surface, the second insulating shield system comprising an insulating material, the second jaw active surface having a second jaw first portion covered by the second insulating shield system and a second jaw second portion at least substantially free from contact with the second insulating shield system, wherein the first and second electrodes are configured to deliver an energy to a tissue.

2. The electrosurgical device of claim 1, wherein the first jaw outside surface is connected to the first jaw first and second side surfaces, and wherein the second jaw outside surface is connected to the second jaw first and second side surfaces.

3. The electrosurgical device of claim 2, wherein the first and second insulating shield systems each comprise at least one of ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and nylon.

4. The electrosurgical device of claim 3, further comprising a first member connected to the first jaw and a second member connected to the second jaw, the electrosurgical device further comprising a tube configured to surround the first and second members to pivot the first jaw with respect to the second jaw.

5. An electrosurgical device comprising:
a pair of jaws including a first jaw and a second jaw, the second jaw being disposed adjacent to the first jaw, the pair of jaws being movable between an open position and a closed position, the first jaw comprising a first electrode and the second jaw comprising a second electrode, the first jaw having a first jaw active surface and the second jaw having a second jaw active surface, the first jaw active surface being disposed adjacent to the second jaw active surface in the closed position, the first jaw including a first jaw outside surface disposed on an opposite side of the first jaw from the first jaw active surface, the first jaw further comprising two first jaw side surfaces, each first jaw side surface of the two first jaw side surfaces connecting the first jaw active surface to the first jaw outside surface, the first jaw also including a first jaw end surface connecting the two first jaw side surfaces;
an actuating member coupled to at least one of the first and second jaws, the actuating member configured to move the pair of jaws between the open position and the closed position;

a first insulating shield system being continuous and having a uniform thickness, the first insulating shield system substantially covering the first jaw outside surface, each of the first jaw side surfaces and covering the first jaw end surface, the first insulating shield system terminating with first jaw lips that partially cover the first jaw active surface, the first jaw active surface having at least a portion substantially free from contact with the first insulating shield system, the first insulating shield system comprising an insulating material, the first jaw lips being disposed a first distance from the second jaw active surface in the closed position, the first jaw active surface being disposed a second distance from the second jaw active surface in the closed position, the first distance being smaller than the second distance, the first jaw lips of the first insulating shield system defining a recess with respect to the first jaw active surface, the recess being displaced inwardly with respect to each of the first jaw side surfaces and the first jaw end surface, wherein the first and second electrodes are configured to deliver and energy to a tissue.

6. The electrosurgical device of claim 5, the electrosurgical device further comprising a second insulating shield system disposed around the second jaw active surface, the second jaw active surface having at least a portion substantially free from contact with the second insulating shield system, the second insulating shield system comprising an insulating material being continuous and having a uniform thickness, the second insulating shield system substantially covering a second jaw outside surface, each of second law side surfaces and covering the second law end surface, the insulating shield system terminating with second law lips that partially cover the second law active surface, the second jaw active surface being recessed with respect to the second jaw lips, the second law lips being disposed a third distance from the first jaw active surface in the closed position, the third distance being smaller than the second distance, the second jaw outside surface being disposed on an opposite side of the second jaw from the second jaw active surface, each second jaw side surface of the two second jaw side surfaces connecting the second jaw active surface to the second jaw outside surface.

7. The electrosurgical device of claim 6, wherein the insulating shield system comprises at least one of ethylene tetrafluoroethylene (ETFE), polytetrafluoroethylene (PTFE), expanded polytetrafluoroethylene (ePTFE), Ethylene ChloroTriFluoroEthylene (ECTFE), polyether ether ketone (PEEK), fluorinated ethylene propylene (FEP), polyvinylidene difluoride (PVDF), polyimide, polyethylene plastic (PEP), and nylon.

8. The electrosurgical device of claim 7, further comprising a first member connected to the first jaw and a second member connected to the second jaw, the electrosurgical device further comprising a tube configured to surround the first and second members to pivot the first jaw with respect to the second jaw.

\* \* \* \* \*